United States Patent
Quist et al.

(10) Patent No.: US 8,191,403 B2
(45) Date of Patent: Jun. 5, 2012

(54) PETROLEUM VISCOSITY MEASUREMENT AND COMMUNICATION SYSTEM AND METHOD

(75) Inventors: Arjan Quist, Schaumburg, IL (US); Ratnesh Lal, Goleta, CA (US); Gregory P. Liesen, Mechanicsville, VA (US); Sunil K. Srivastava, Oak Brook, IL (US)

(73) Assignee: Richmond Chemical Corporation, Oak Brook, IL (US)

( * ) Notice: Subject to any disclaimer, the term of this patent is extended or adjusted under 35 U.S.C. 154(b) by 483 days.

(21) Appl. No.: 12/057,016

(22) Filed: Mar. 27, 2008

(65) Prior Publication Data

US 2008/0289400 A1    Nov. 27, 2008

Related U.S. Application Data

(60) Provisional application No. 60/908,213, filed on Mar. 27, 2007.

(51) Int. Cl.
*G01N 33/26* (2006.01)
(52) U.S. Cl. ..................................... 73/53.05
(58) Field of Classification Search ............. 73/1.02, 73/53.05, 54.41, 64.53; 850/57
See application file for complete search history.

(56) References Cited

U.S. PATENT DOCUMENTS

| | | | |
|---|---|---|---|
| 4,802,493 A | 2/1989 | Maganias |
| 4,809,707 A | 3/1989 | Kraft et al. |
| 4,819,657 A | 4/1989 | Kraft et al. |
| 4,966,159 A | 10/1990 | Maganias |
| 5,021,364 A | 6/1991 | Akamine et al. |
| 5,027,826 A | 7/1991 | Fishman |
| 5,041,390 A | 8/1991 | Skov et al. |
| 5,076,282 A | 12/1991 | Fishman et al. |
| 5,097,810 A | 3/1992 | Fishman et al. |
| 5,098,831 A | 3/1992 | Skov et al. |
| 5,104,620 A | 4/1992 | Wiley et al. |

(Continued)

FOREIGN PATENT DOCUMENTS

WO    WO 2004/042376    5/2004

(Continued)

OTHER PUBLICATIONS

Arntz, et al. (2003) "Label-free protein assay based on a nanomechanical cantilever array" *Nanotechnology*, 14, 86-90.

(Continued)

*Primary Examiner* — John Fitzgerald
(74) *Attorney, Agent, or Firm* — Avani C. Macaluso; McDermott Will & Emery, LLP

(57) ABSTRACT

The disclosure presents an apparatus and method for measuring viscosity of a lubricating oil. The apparatus has a piezoresistive cantilever sensor for sensing a first oil viscosity parameter. The sensor has a cantilever having a pressure receiving portion for receiving pressure exerted by the lubricating oil as the lubricating oil comes into contact with the pressure receiving portion. The cantilever also has first and second resistive portions in electrical communication with a first lead and a second lead, respectively, which are in electrical communication with an electrical circuit amplification element, for creating an output signal indicative of a change in the resistive characteristics of the first and second resistive portions of the cantilever as the lubricating oil comes into contact with the pressure receiving portion. The output signal can be used for determining oil viscosity. A processor and memory compare the output signal value with a stored resistance value to provide information relating to the quality of the lubricating oil.

23 Claims, 9 Drawing Sheets

U.S. PATENT DOCUMENTS

| | | | |
|---|---|---|---|
| 5,116,731 A | 5/1992 | Wilhelms | |
| 5,139,029 A | 8/1992 | Fishman et al. | |
| 5,154,181 A | 10/1992 | Fishman | |
| 5,156,810 A | 10/1992 | Ribi | |
| 5,179,959 A | 1/1993 | Fishman et al. | |
| 5,335,670 A | 8/1994 | Fishman | |
| 5,386,720 A * | 2/1995 | Toda et al. | 73/105 |
| 5,583,286 A * | 12/1996 | Matsuyama | 73/105 |
| 5,588,441 A | 12/1996 | Fishman | |
| 5,605,160 A | 2/1997 | Fishman | |
| 5,614,167 A | 3/1997 | Hansen et al. | |
| 5,714,338 A | 2/1998 | Wai Fei et al. | |
| 5,719,324 A | 2/1998 | Thundat et al. | |
| 5,735,288 A | 4/1998 | Fishman | |
| 5,807,758 A | 9/1998 | Lee et al. | |
| 5,908,981 A | 6/1999 | Atalar et al. | |
| 5,931,794 A | 8/1999 | Pitesky | |
| 6,016,686 A | 1/2000 | Thundat | |
| 6,077,229 A | 6/2000 | Pitesky | |
| 6,079,255 A * | 6/2000 | Binnig et al. | 73/105 |
| 6,159,742 A | 12/2000 | Lieber et al. | |
| 6,212,939 B1 | 4/2001 | Thundat | |
| 6,221,027 B1 | 4/2001 | Pitesky | |
| 6,258,041 B1 | 7/2001 | Pitesky | |
| 6,269,685 B1 | 8/2001 | Oden | |
| 6,289,717 B1 | 9/2001 | Thundat et al. | |
| 6,311,557 B1 | 11/2001 | Davis et al. | |
| 6,319,467 B1 | 11/2001 | McLernon et al. | |
| 6,322,520 B1 | 11/2001 | Baik | |
| 6,523,392 B2 | 2/2003 | Porter et al. | |
| 6,537,499 B1 | 3/2003 | Bernard et al. | |
| 6,575,020 B1 | 6/2003 | de Charmoy Grey et al. | |
| 6,597,499 B2 | 7/2003 | Kawano et al. | |
| 6,664,540 B2 * | 12/2003 | Shimizu et al. | 850/52 |
| 6,682,927 B2 | 1/2004 | Meyer et al. | |
| 6,689,569 B2 | 2/2004 | Vojdani | |
| 6,695,470 B1 | 2/2004 | Berndofer et al. | |
| 6,705,154 B2 | 3/2004 | Nakayama et al. | |
| 6,718,819 B2 | 4/2004 | Schoess | |
| 6,734,287 B1 | 5/2004 | Lawton et al. | |
| 6,743,408 B2 | 6/2004 | Lieber et al. | |
| 6,751,018 B2 | 6/2004 | Kawano et al. | |
| 6,759,653 B2 | 7/2004 | Nakayama et al. | |
| 6,763,705 B1 | 7/2004 | Thundat et al. | |
| 6,787,308 B2 | 9/2004 | Balasubramanian et al. | |
| 6,805,839 B2 | 10/2004 | Cunningham et al. | |
| 6,819,484 B2 | 11/2004 | Aono et al. | |
| 6,823,717 B2 | 11/2004 | Porter et al. | |
| 6,854,317 B2 | 2/2005 | Porter et al. | |
| 6,854,338 B2 * | 2/2005 | Khuri-Yakub et al. | 73/861.27 |
| 6,858,398 B2 | 2/2005 | Vojdani | |
| 6,897,015 B2 | 5/2005 | Henderson et al. | |
| 6,901,788 B2 | 6/2005 | Han et al. | |
| 6,917,865 B2 | 7/2005 | Arai et al. | |
| 6,952,951 B2 | 10/2005 | Jakoby | |
| 7,017,662 B2 * | 3/2006 | Schultz et al. | 166/254.2 |
| 7,046,451 B2 | 5/2006 | Mandai et al. | |
| 7,105,301 B2 | 9/2006 | Su et al. | |
| 7,141,385 B2 | 11/2006 | Bottomley et al. | |
| 7,168,294 B2 | 1/2007 | Porter et al. | |
| 7,177,018 B2 | 2/2007 | Seeley | |
| 7,458,265 B2 * | 12/2008 | Shih et al. | 73/579 |
| 7,555,938 B2 * | 7/2009 | Bargatin et al. | 73/64.53 |
| 7,671,511 B2 * | 3/2010 | Battiston | 310/316.01 |
| 2001/0020680 A1 | 9/2001 | Cunningham et al. | |
| 2001/0028033 A1 * | 10/2001 | Shimizu et al. | 250/309 |
| 2002/0083771 A1 * | 7/2002 | Khuri-Yakub et al. | 73/589 |
| 2002/0114987 A1 | 8/2002 | Oscarsson et al. | |
| 2003/0010097 A1 | 1/2003 | Porter et al. | |
| 2003/0068655 A1 | 4/2003 | Bottomley et al. | |
| 2003/0138801 A1 | 7/2003 | Oscarsson et al. | |
| 2003/0209058 A1 | 11/2003 | Merrill | |
| 2004/0029108 A1 | 2/2004 | Bottomley et al. | |
| 2004/0080319 A1 | 4/2004 | Merrill | |
| 2004/0194534 A1 | 10/2004 | Porter et al. | |
| 2004/0211243 A1 | 10/2004 | Porter et al. | |
| 2004/0222480 A1 | 11/2004 | Weisbuch et al. | |
| 2005/0039523 A1 | 2/2005 | Niwa et al. | |
| 2005/0051515 A1 * | 3/2005 | Nam | 216/27 |
| 2005/0150691 A1 * | 7/2005 | Schultz et al. | 175/57 |
| 2005/0195407 A1 | 9/2005 | Nordin et al. | |
| 2005/0201899 A1 | 9/2005 | Weisbuch | |
| 2005/0214160 A1 | 9/2005 | Weisbuch et al. | |
| 2005/0244820 A1 | 11/2005 | Su et al. | |
| 2006/0032289 A1 | 2/2006 | Pinnaduwage et al. | |
| 2006/0053871 A1 | 3/2006 | Porter et al. | |
| 2006/0230817 A1 | 10/2006 | Schilowitz et al. | |
| 2007/0033990 A1 * | 2/2007 | Grey et al. | 73/53.01 |
| 2007/0089515 A1 * | 4/2007 | Shih et al. | 73/579 |
| 2007/0117217 A1 | 5/2007 | Lal et al. | |
| 2007/0238184 A1 | 10/2007 | Lal et al. | |
| 2008/0011058 A1 | 1/2008 | Lal et al. | |
| 2008/0068000 A1 * | 3/2008 | Bargatin et al. | 324/76.11 |
| 2008/0136291 A1 * | 6/2008 | Battiston | 310/319 |
| 2008/0293148 A1 * | 11/2008 | Kim et al. | 436/86 |
| 2009/0301196 A1 * | 12/2009 | Wang et al. | 73/579 |

FOREIGN PATENT DOCUMENTS

| | | |
|---|---|---|
| WO | WO 2006/138161 | 12/2006 |
| WO | WO 2007/109323 | 9/2007 |

OTHER PUBLICATIONS

Baselt, California Institute of Technology (1993), "The tip sample interaction in atomic force microscopy and its implications for biological applications," (1993) pp. 6-7.

Baselt et al. (1996) A Biosensor based on Force Microscope Technology, *J. Vac. Science Tech.* B., vol. 14, No. 2 (5pp).

Belaubre, P. et al., "Fabrication of biological microarrays using microcantilevers" Applied Physics Letters, May 5, 2003,82(18):3122-3124.

Fritz et al. (2000). Translating biomolecular recognition into nanomechanics. Science 288:316-318.

Lo, et al., "Organic and inorganic contamination on commercial AFM cantilevers" Langmuir, 1999, 15:6522-6526.

Lutwyche, et al., "5X5 2D AFM cantilever arrays a first step toward Terabit storage device" Sensors and Actuators, 1999, 73:89-94.

Tong et al. (2005) "Compressive Properties of Dense *Vertically Aligned Multi-walled Carbon Nanatube arrays,* " *Proc. Of NAN02005 ASME Integrated Nanosystems: Design, Synthesis & Applications*; Sep. 14-16, 2005, p. 3.

* cited by examiner

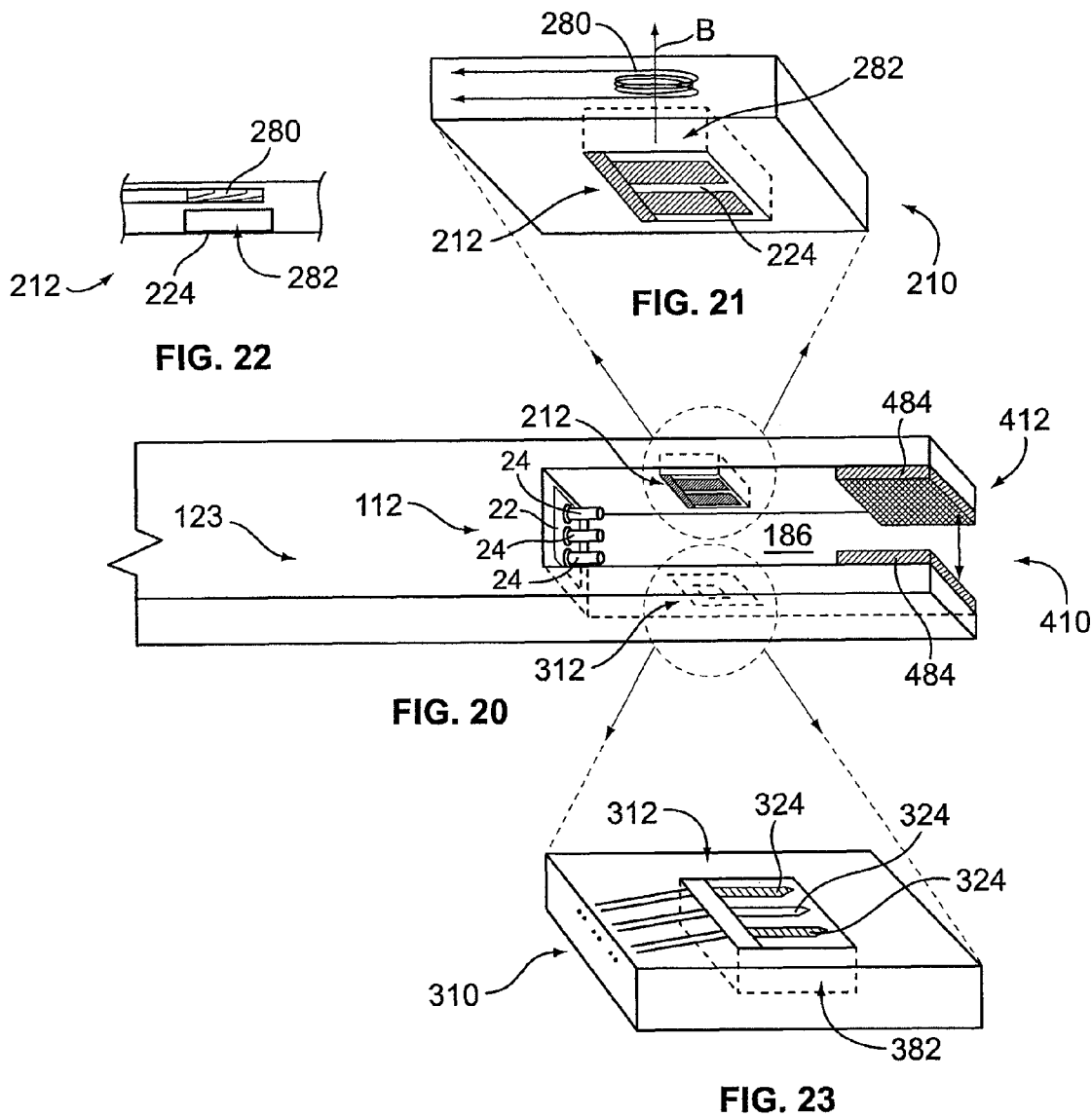

PETROLEUM VISCOSITY MEASUREMENT AND COMMUNICATION SYSTEM AND METHOD

CROSS-REFERENCE TO RELATED APPLICATIONS

This application claims priority from U.S. Patent Application Ser. No. 60/908,213 entitled "Petroleum Viscosity Measurement and Communication System and Method", filed Mar. 27, 2007, which is incorporated herein by reference in its entirety.

TECHNICAL FIELD

The present invention is related to a system and method for measuring viscosity of a liquid, such as for example petroleum. More particularly, the present invention relates to a system and method for measuring attributes of petroleum, analyzing the attributes to determine petroleum viscosity, and communicating related information to target locations.

BACKGROUND OF THE INVENTION

Several prior systems and methods exist to measure and utilize viscosity measurements of motor oil an automobile and provide a driver with information on whether the motor oil should be changed. Specifically, U.S. Pat. No. 6,695,470 B1 to Berndorfer et al. is directed to an apparatus and method for determining a change in the viscosity of a fluid. The apparatus and method includes heating a portion of the liquid and determining the rise time and average velocity of the heated portion between a heat source and a sensor, to determine viscosity A baseline rise time and baseline average velocity are used to compare to the rise time and average velocity to determine the change in viscosity of the fluid, and to indicate whether the fluid should be changed. This indication can be shown on the control panel of an automobile.

U.S. Pat. No. 6,952,951 B2 to Jacoby is directed to measuring viscosity of a liquid as a function of temperature. The method and device measures viscosity using a viscosity sensor and measures temperature using a temperature sensor. The method and device comes to a conclusion on the temperature and on the viscosity at a specified point in time, and discards and/or corrects one of these measured values as a result of the degree of inhomogeneity in the temperature distribution. An absolute value of the temporal difference quotient of the temperature measured value is ascertained as a measure of the inhomogeneity of the temperature of the liquid. A certain threshold indicates an acceptable reduction in temporal difference or temperature gradient.

U.S. Pat. No. 6,901,788 B2 to Han et al. is directed to an oil change sensing system for an internal combustion engine. An oil pressure sensor located in an oil sump senses oil pressure, a temperature sensor senses temperature of the oil, and a revolutions per minute (RPM) sensor senses RPM speed of the motor, at specific times and for new and/or old oil. Multiple readings are taken. When the oil temperature exceeds 80 degrees Celsius at an idle speed, the system has an engine control module which uses this information to calculate viscosity for the oil and compare the viscosity to preexisting old or new old viscosity data from actual readings previously taken or from look-up tables, as a function of at least one of the oil pressure, oil temperature and engine RPM.

U.S. Pat. No. 6,917,865 B2 to Arai et al. is directed to an engine oil degradation determining system. A crankshaft angle sensor detects engine rotational speed of an internal combustion engine, and a control unit calculates a cumulative revolution number which is indicative of the degradation level of the engine oil. An oil level detector detects the oil level or the engine oil. If the detected oil level is lower than a predetermined lower level while the engine is stopped, or when the engine is started and the oil level is higher than a predetermined higher limit, the calculated cumulative revolution number is corrected in the direction of indicating a lower degradation level.

U.S. Pat. No. 6,718,819 B2 to Schoess is directed to an apparatus for determining the condition of engine lubricating oil. The apparatus includes a sensor having a plurality of spaced apart electrode pairs on a nonconductive polymer film. The sensor averages signal output to reduce operational electromagnetic interference noise. A forcing function waveform reactive circuit is applied to the sensor as a common voltage potential. The output current from the sensor is then transformed to an equivalent voltage and compared to predetermined values to determine the condition of the oil, and will trigger a trouble code if the equivalent voltage falls within a predetermined range.

The above systems, apparatuses, and methods include bulky sensors which are sometimes unreliable, in part due to the limited information which such sensors are able to provide for determining related parameters. These parameters may be indicative of viscosity through the combination of such parameters with other measured parameters through calculations, look up tables, and other mechanisms. These mechanisms and parameters are a product of the measured or sensed information and thus have inherent potential drawbacks associated with such measured or sensed information. The sensors themselves also have significant limitation on where such sensors can be placed and utilized based on the construction of such sensors and the limitations of manufacturers in creating reliable sensors for measuring or sensing necessary information for parameters used in the calculation or determination of the viscosity of a liquid.

The present invention is provided to solve or address these and other problems.

SUMMARY OF INVENTION

The present apparatus and method measures viscosity of a lubricating oil. The apparatus has a piezo-resistive cantilever sensor for sensing a first oil viscosity parameter, such as a parameter which can be used to calculate viscosity or look up viscosity of the lubricating oil. The first oil viscosity parameter can also be a direct measure of viscosity depending on the sensor construction, any circuits attached to the sensor or made a part thereof, or other configuration of the apparatus.

The sensor has a cantilever, which in turn has a pressure receiving portion or region. The pressure receiving portion receives pressure exerted by the lubricating oil as the lubricating oil comes or flows into contact with the pressure receiving portion. The cantilever also has a first resistive portion or region, which is in electrical communication with the pressure receiving portion. The cantilever also has a second resistive portion or region in electrical communication with the pressure receiving portion.

The sensor also has a first lead in electrical communication with the first resistive portion, and a second lead in electrical communication with the second resistive portion. The apparatus also has an electrical circuit amplification element, such as a Wheatstone bridge, in electrical communication with the first lead and the second lead for creating an output signal indicative of a change in the resistive characteristics of the first and second resistive portions of the cantilever as the lubricating oil comes into contact with the pressure receiving portion. The output signal can then converted into a parameter or used directly as a parameter for determining oil viscosity.

The apparatus also has a microprocessor or microcomputer which is in communication with the electrical circuit amplification element and receives an amplified output signal indicative of the output signal. The processor is in communication with the electrical circuit amplification element and receives and stores the output signal. The processor includes a memory associated therewith for receiving and storing the output signal. The processor also determines the quality of the lubricating oil by comparing the output signal with a stored resistance value in the memory.

The apparatus can also have a user interface device, such as an in-dash automobile display screen, an in-dash digital or analog readout, and/or a Personal Digital Assistant (PDA), which is in communication with the processor for receiving and communicating a lubricating oil quality signal through the interface device to the driver or user of such interface, in response to the processor determining quality of the lubricating oil.

In one embodiment, the piezo-resistive cantilever sensor can be mounted to a motor oil dip stick for insertion into the dip stick receiving tube of an automobile engine, and into the automobile engine oil reservoir for allowing the lubricating oil for the automobile to come into contact with or flow into contact with the cantilever of the sensor.

In another embodiment, the apparatus can have a radio frequency (RF) transmitter that is in electrical communication with the electrical circuit amplification element for receiving the output signal from the electrical circuit amplification element, and for communicating the amplified output signal to the processor. Likewise, the apparatus can have an RF receiver in electrical communication with the processor for receiving the output signal from the RF transmitter, and for communicating the output signal to the processor.

In a further embodiment, the apparatus can have a network interface for interfacing with a communication network, such as the Internet, for receiving the lubricating oil quality signal and for transmitting the lubricating oil quality signal to the communications network. The user interface device, such as a PDA having a wireless interface and supporting software for interfacing and communicating with the communications network, can receive the lubricating oil quality signal from the communication network and communicate the lubricating oil quality signal through the interface, such as through a display screen.

The lubricating oil quality signal, value and/or information displayed or communicated to a driver or user can include various significant information. Specifically, the lubricating oil quality information can include "change oil now" information, information regarding the time until an oil change is needed, information regarding the driving distance until an oil change is needed, viscosity information, service station information, and/or coupon information, among other types of useful content.

In a further embodiment, an intermediary server can be used for receiving the lubricating oil quality signals from various processors determining the oil quality signals. The server can determine whether to send service station information and/or coupon information to respective user interface devices. The server can determine to which user interface device to send the service station information and/or coupon information based on the content of the lubricating oil quality signal, such as an association of each signal with each user interface device based on the content of each of the lubricating oil quality signals. The server transmits service station information and/or coupon information to respective user interface devices when the determination indicates that the content comprises change oil now information, the content comprises a time until oil change is needed information which is less than a predetermined time, and/or the content comprises distance until oil change is needed information which is less than a predetermined distance.

In other embodiments, the apparatus can be configured to measure other properties of the lubricating oil by a reaction of the cantilever to the property of the lubricating oil. Such properties include the amount of magnetic particles in the lubricating oil, the amount of a specific chemical in the lubricating oil (including but not limited to water and ethanol), and the pH of the lubricating oil.

The present invention also includes an apparatus for measuring the capacitance of a lubricating oil. The apparatus includes a sensor having a pair of parallel, spaced conductive plates, positioned so the lubricating oil flows between the plates and a capacitance measurement device connected to the sensor for measuring the capacitance of the lubricating oil.

The present invention also includes a method of calibrating an apparatus as described above for measuring the viscosity of a lubricating oil, including the steps of positioning the piezo-resistive cantilever sensor in a flow-line of a calibration oil having a known viscosity value associated therewith, flowing the calibration oil into the piezo-resistive cantilever sensor, measuring an output signal value for the calibration oil, storing an output signal value for the calibration oil, and storing the known viscosity value for the calibration oil.

In one embodiment, the method also includes the steps of retrieving the output signal value for the calibration oil, retrieving the known viscosity value for the calibration oil, calculating the viscosity of the lubricating oil using the output signal value for the calibration oil and the known viscosity value for the calibration oil for determining the quality of the lubricating oil.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 20 is a schematic view of a dipstick having a viscosity sensor, a magnetic particle detection sensor, a capacitance sensor, and a chemical detection sensor of the present invention;

FIG. 21 is a magnified view of the magnetic particle detection sensor of FIG. 20;

FIG. 22 is a cross-sectional view of the magnetic particle detection sensor of FIG. 21; and FIG. 23 is a magnified view of the chemical detection sensor of FIG. 20.

DETAILED DESCRIPTION

Figure 1:
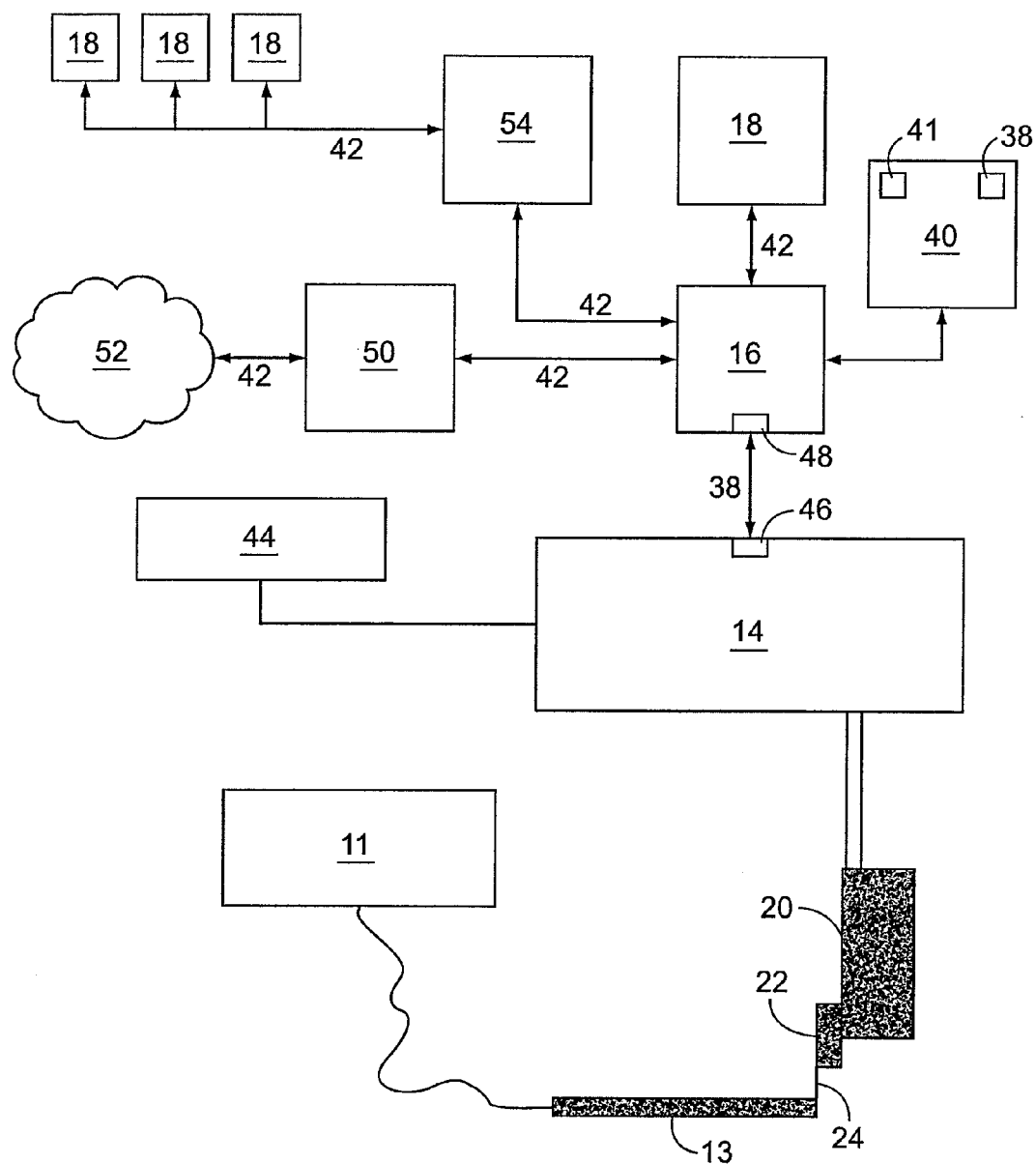
FIG. 1 is a schematic diagram of one embodiment of an apparatus of the present invention for measuring the viscosity of a fluid.

While this invention is susceptible to embodiment in many different forms, there are shown in the drawings and herein described in detail preferred embodiments with the understanding that the present disclosure is considered to provide an example of the principles of the invention, and is not intended to limit the broad aspect of the invention to the embodiments illustrated.

Figure 2:
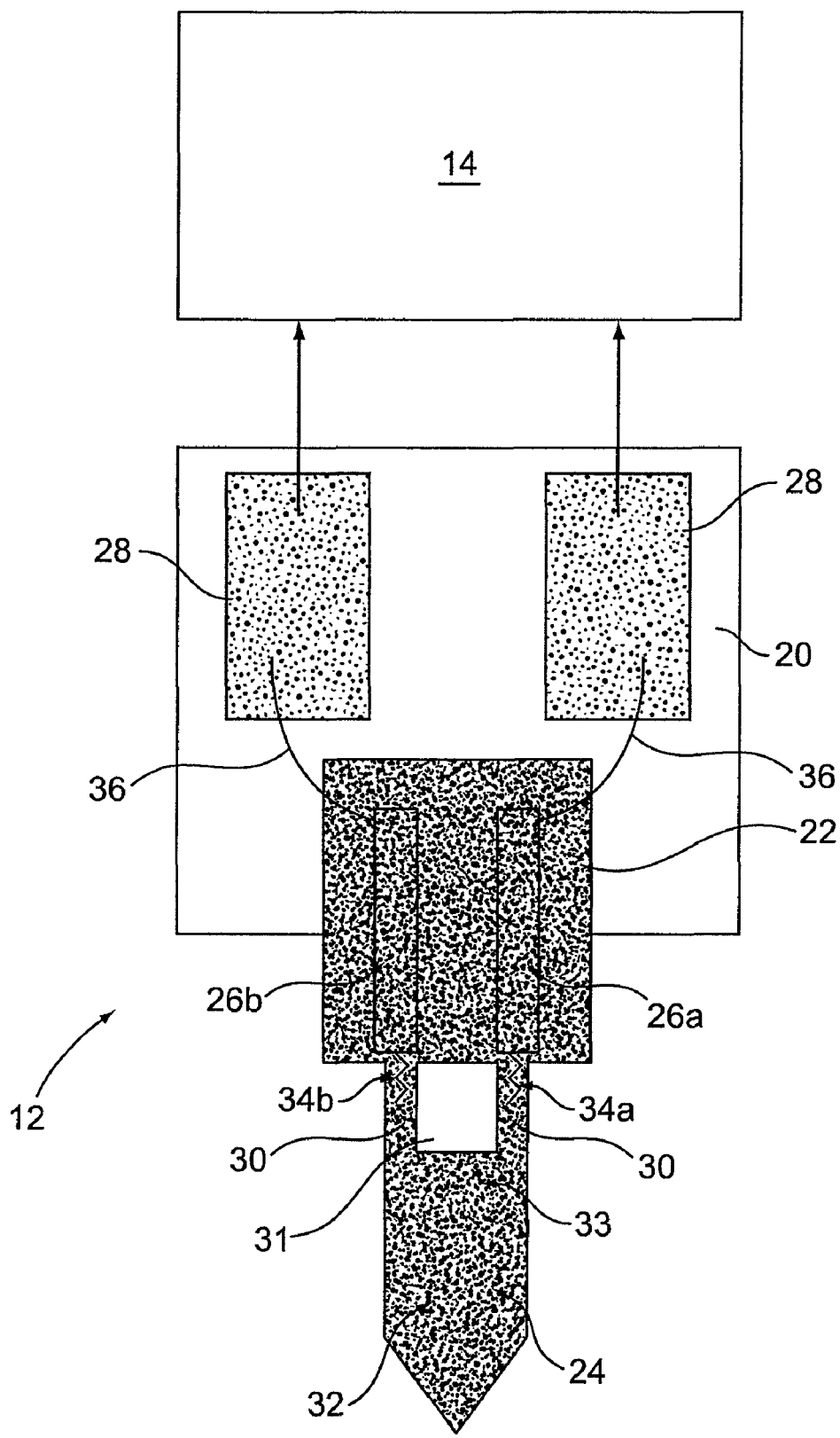
FIG. 2 is a magnified plan view of a sensor of the apparatus of FIG. 1.

Referring to the figures, and initially to FIGS. 1 and 2, an apparatus 10 for measuring the viscosity of a fluid 11 is shown. The apparatus 10 generally includes a sensor 12, an electrical circuit amplification element 14, a processor 16 in communication with the electrical circuit amplification element 14, and a user interface device 18 in communication with the processor 16. A portion of the sensor 12 extends into a flow path 13 of the fluid 11 to sense one or more parameters of the fluid 11. It is understood that connections and communications between the components of the apparatus 10, including the amplification element 14, the processor 16, and the interface device 18, may be wired or wireless connections and communications.

Figure 17:
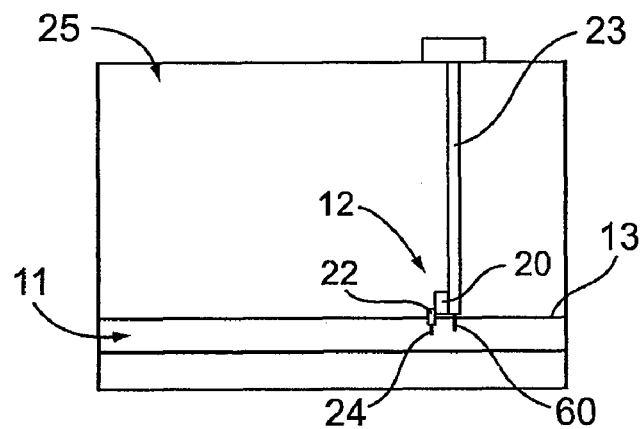
FIG. 17 is a schematic diagram of a sensor of an apparatus of the present invention used in connection with an automobile.

The sensor 12 is configured for sensing properties or parameters of the lubricating oil, such as viscosity. The preferred sensor 12 is illustrated in FIG. 2, and is a piezo-resistive cantilever sensor including a base 20, a cantilever chip 22 mounted on the base 20 that has a narrow cantilever 24 at the tip, and conductive leads 26 in electrical communication with the cantilever chip 22. In a preferred embodiment, illustrated in FIG. 17, the sensor 12 is mounted to a motor oil dipstick 23 for insertion into an automobile engine 25 to measure a viscosity parameter of lubricating oil 11. Preferably, the sensor is extremely small, and the cantilever 24 has a width of less than 30 nm, or at least of a similar order of magnitude.

The base 20 is preferably a non-conductive ceramic plate that serves as a mount for the cantilever chip 22 and the cantilever 24. In a preferred embodiment, the base 20 is mounted to the motor oil dipstick 23. Generally, the base 20 is larger than the cantilever chip 22 to provide stable and sturdy support, but this arrangement is not necessary. In other embodiments, the base 20 may be differently configured, and may be configured to be mounted on another structure. The base 20 also preferably has two conductive contacting pads 28 mounted on or within the base 20 to serve as electrical connections between the cantilever chip 22 and the amplification element 14. Preferably, the pads 28 are deposited on the ceramic plate and are at least partially made of gold. However, in other embodiments, the pads 28 may be made of a different material. The base 20 may be made of a different material, but preferably, the base 20 is non-conductive.

Figure 16:
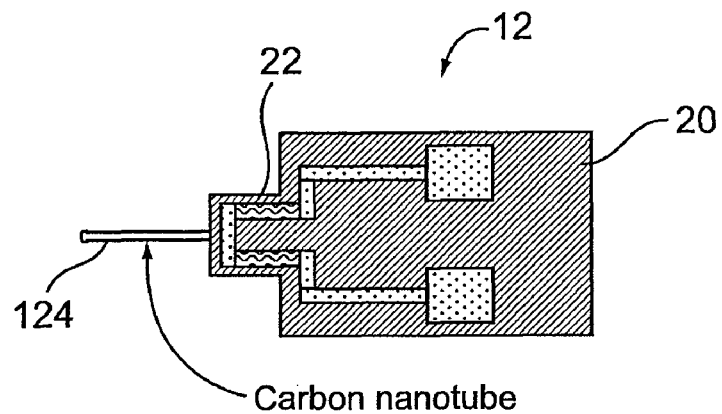
FIG. 16 is a top view of an alternate embodiment of a sensor of the present invention, having a carbon nanotube cantilever.

The cantilever chip 22 is preferably a silicon chip that is connected to the base 20 at one end and has a cantilever 24 at the other end. At least a portion of the cantilever 24 is preferably implanted or doped with boron atoms, making the cantilever 24 piezo-resistive. The implanted boron atoms also provide a current path 33 through a portion of the cantilever 24. Because the cantilever 24 is piezo-resistive, distortion of the crystal lattice, such as by bending the cantilever 24, will alter the resistivity of the distorted portion of the cantilever 24. A portion of the chip 22 may also be implanted with boron atoms to achieve the same effects. Preferably, the cantilever 24 is extremely narrow and is somewhat "U-shaped," and is connected to the chip 22 by two legs 30 having a slot 31 therebetween. The U-shape of the cantilever 24 defines the current path 33 through the cantilever 24, such that electrical current flows through the current path 33 into the cantilever 24 through one leg 30 and out of the cantilever 24 through the other leg 30. Preferably, the cantilever 24 is also silicon and is integral with the chip 22. In other embodiments, the chip 22 and cantilever 24 may be made from a material other than silicon. Further, the cantilever 24 may be made of a different material than the chip 22, such as a carbon nanotube cantilever 124, as shown in FIG. 16. In still further embodiments, the chip 22 may be configured to function as the cantilever 24, and may not include the cantilever 24 at the tip as described above.

In a general sense, the cantilever 24 contains a pressure receiving portion 32 and first and second resistive portions 34. The resistive portions 34 are preferably in electrical communication with the pressure receiving portion 32, and the current path 33 passes through at least a portion of the pressure receiving portion 32. The pressure receiving portion 32 receives pressure exerted by the lubricating oil 11 as the oil 11 comes into contact with the pressure receiving portion 32. In a preferred embodiment, the pressure receiving portion 32 is located at the free end of the cantilever 24, which extends into the flow path 13 of the lubricating oil 11. The resistive portions 34 are implanted with boron atoms, and are thus piezo-resistive and lie within the current path 33 and provide electrical resistance as the current flows through. Each of the resistive portions 34 are preferably piezo-resistive, so the resistivity of the resistive portions 34 changes as the cantilever 24 bends. The legs 30 connecting the cantilever 24 to the chip 22 are narrower than the rest of the cantilever 24, and are consequently less resistant to bending. Further, bending stresses are often more heavily concentrated near the fixed end of a cantilever structure, so the legs 30 experience greater deformation and stress than the other portions of the cantilever 24. Thus, the resistive portions 34 are preferably located in the legs 30, because the bending and resultant distortion of the crystal lattice (causing changes in electrical resistance) is generally greater in the legs 30 than at other areas of the cantilever chip 22.

As illustrated in FIG. 2, two electrical leads 26 are mounted either on or within the chip 22. The electrical leads 26 are generally made of a metal or combination of metals, and are preferably made at least partially of aluminum or a chromium/gold alloy. One of the leads 26a is in electrical communication with the first resistive portion 34a, and the other lead 26b is in electrical communication with the second resistive portion 34b. Thus, in the preferred embodiment illustrated in FIG. 2, each of the leads 26 is in electrical communication with one of the legs 30 of the cantilever chip 22. Each of the leads 26 is also preferably electrically connected to one of the gold pads 28 located on the base 20 by a thin gold wire 36. This arrangement allows for a simple electrical readout.

Generally, the electrical circuit amplification element 14 is in electrical communication with at least one of the leads 26. Preferably, the amplification element 14 is connected to the lead(s) 26 through one or both of the pads 28 on the base 20, but may alternately be connected in a different manner. Additionally, the amplification element 14 is configured for creating an amplified output signal 38 indicative of a change in the resistive characteristics of the resistive portions 34 as the lubricating oil comes into contact with the pressure receiving portion 32. In a preferred embodiment, the electrical circuit amplification element 14 includes a Wheatstone bridge, and the resistance of the sensor 12 constitutes one of the resistors of the Wheatstone bridge. Thus, as the resistance of the sensor 12 changes by the bending or deflection of the cantilever 24, the amplification element detects such change and creates a voltage output. In this way, deflection of the cantilever 24 is generally recorded as the voltage output of the amplification element 14, and the output signal 38 preferably either is equivalent to the voltage output or is indicative of the voltage output (such as an amplified form thereof). In one embodiment, the amplification element 14 is integrally fabricated within the chip 22. In other embodiments, the amplification element 14 may be another type of element capable of detecting changes in resistance. In another embodiment, the three other resistors of the Wheatstone bridge (the cantilever 24 being the fourth) can be incorporated on the chip 22 by ion implantation. In still another embodiment, two of the other resistors of the Wheatstone bridge can be incorporated on the chip 22, while one resistor is external for calibration and offset purposes.

The electrical circuit amplification element 14 is preferably connected to a power supply 44 for driving current through the amplification element 14 and the sensor 12, including the resistive portions 34 of the sensor 12. The power supply 44 can be a battery, such as a automobile battery, which is advantageous if the apparatus 10 is contained within an automobile. A preferred embodiment of the apparatus 10 utilizes a 15V power supply 44.

Figure 19:
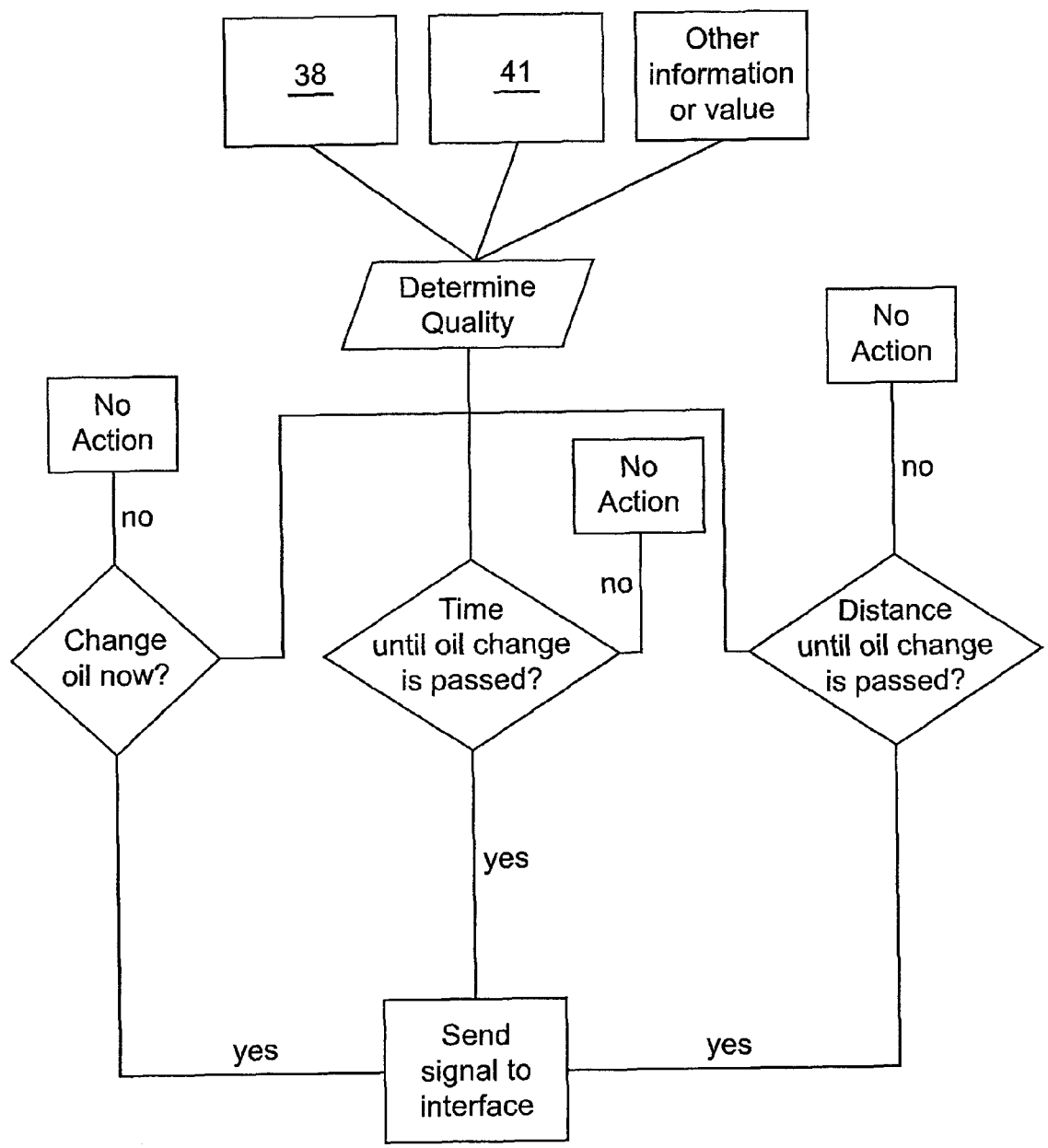
FIG. 19 is a diagram of decision making processes within an apparatus of the present invention

The apparatus 10 also has a microprocessor or microcomputer 16 which is in communication with the electrical circuit amplification element 14 and receives an amplified output signal 38 indicative of the output signal 38. The processor 16 is in communication with the electrical circuit amplification element 14 and receives and stores the output signal 38. The processor 16 includes a memory 40 associated therewith for receiving and storing the output signal 38. The processor 16 also determines the quality of the lubricating oil 11 by comparing the output signal 38 with a stored resistance value 41 in the memory 40. Preferably, the output signal value 38 is used in determining the quality of the lubricating oil by comparing the output signal value 38 with the stored resistance value 41, such as a known resistance value representative of when of a lubricating oil 11 should be changed, as illustrated in FIG. 19. Other resistance values can be used as well, such as a resistance value which indicates that the lubricating oil 11 should be changed after a certain distance such as 1000 miles, or should be changed after a certain passage of time, such as in two months. A plurality of such predetermined values can be stored in the memory 40 for use in making such determinations. The determination of the quality of the lubricating oil 11 may also require the use of a temperature of the lubricating oil 11 for which the determination is being made.

The apparatus can also have a user interface device 18, such as an in-dash automobile display screen, an in-dash digital or analog readout, and/or a Personal Digital Assistant (PDA), which is in communication with the processor 16 for receiving and communicating a lubricating oil quality signal 42 through the interface device to the driver or user of such interface 18, in response to the processor 16 determining quality of the lubricating oil 11. The interface device 18 can communicate to the user various information about the quality of the lubricating oil 11, as well as other information.

The connection and communication between the processor 16, the interface device 18, and other components of the apparatus 10 may be embodied in a variety of different ways. As stated above, the connections and communications between the components of the apparatus 10 may be either wired or wireless connections and communications. In a preferred embodiment, the apparatus 10 is used with an automobile, and the processor 16 and the interface device 18 are contained within the automobile. The interface device 18 may contain a light or other visual indicator, or may generate an audible signal. Alternately, the interface device 18 may be at a remote location, receiving wireless communications from the processor 16. The apparatus 10 may additionally include a plurality of user interface devices 18, all connected to the processor 16, which may display identical or different lubricating oil quality signals 42 to any number of users. In another embodiment, the processor 16 and the interface device 18 are contained together within a single computer, and the interface device 18 is a monitor or other visual display or indicator. In a further embodiment, the processor 16 and the interface device 18 both in remote locations, and the processor 16 receives the output signal 38 via wireless communication. Still further embodiments are possible, making use of wired or wireless connections and communications.

The lubricating oil quality signal 42 is preferably in a format containing content that is readily observable and comprehensible by a user or other desired person. Additionally, the apparatus 10 may use a plurality of lubricating oil quality signals 42. A lubricating oil quality signal 42 may include content of "change oil now" information indicating at least in part that the lubricating oil 11 should be changed soon or as soon as possible. The lubricating oil quality information 42 can include "time until oil change is needed" information indicating at least in part an amount of time that can safely pass without changing the lubricating oil (which would have a translation factor for an average or realistic high end number of miles which may be traveled by an automobile with the lubricating oil for such a time period). The lubricating oil quality information 42 can also include "distance until oil change is needed" information indicating at least in part a linear or angular distance, such as miles, kilometers, radians, or some other distance. The lubricating oil quality information 42 can also include viscosity information, such as viscosity or a parameter used in calculating viscosity. The lubricating oil quality information 42 can also include "service station" information indicating at least the name, location, and contact information such as a phone number for a service station which can change the lubricating oil. The lubricating oil quality information 42 can also include "coupon" information providing a coupon, such as a discount for a lubricating oil change for a service station or chain of service stations, which can be printed out for use in obtaining the discount. A code could also be provided for use in obtaining the discount, for proof of entitlement to the coupon or discount.

The apparatus 10 may include an intermediary server 54 for receiving one or more lubricating oil quality signals 42, determining whether to send service station information and/or coupon information to respective user interface devices 18 associated with each user interface device 18 based on the content of each of the lubricating oil quality signals 42, and transmitting service station information and/or coupon information to respective user interface devices 18 if desirable. The intermediary server 54 may transmit such service station information and/or coupon information to user interface devices 18 when the determination indicates that the content includes "change oil now" information, the content includes information regarding the time until an oil change is needed which is less than a predetermined time, and/or the content includes information regarding the driving distance until an oil change is needed which is less than a predetermined distance. The intermediary server 54 may also transmit a lubricating oil quality signal 42 when the determination indicates that the content includes viscosity information which is not within a predetermined range. This process is illustrated in FIG. 19.

In a preferred embodiment, an RF transmitter 46 is in electrical communication with the electrical circuit amplification element 14. The RF transmitter 46 receives the output signal 38 from the amplification element 14 and communicates the output signal 38 to the processor 16. Additionally, an RF receiver 48 is in electrical communication with the processor 16. The RF receiver 48 receives the output signal 38 from the RF transmitter 46 and communicates the output signal 38 to the processor. Depending on the arrangement, analog to digital (A/D) or digital to analog (D/A) conversion may take place before the RF communication. Again, depending on the implementation, an A/D or D/A conversion may take place after the RF communication, and before the output signal or signal value is received by the processor.

The apparatus 10 may also include a network interface 50 for interfacing with a communication network 52, such as the Internet or a local area network (LAN). The network interface 50 receives the lubricating oil quality signal 42 and transmits the lubricating oil quality signal 42 to the communication network 52. Preferably, the user interface device 18 receives the lubricating oil quality signal 42 from the communication network 52 and communicates the lubricating oil quality signal 42 through the interface device 18.

The viscosity of a fluid is also dependent on temperature. Therefore, the apparatus 10 may also include a thermistor 60 or other temperature sensor, which is preferably also attached to the dipstick 23. This allows for accurate measurement of viscosity at all times, due to the proximity of both temperature and viscosity measurement. As for the viscosity communication, communication of temperature would be from the dipstick 23 to the dashboard via the vehicle computer system. Appropriate algorithms can be used to convert the relative viscosity measurements and temperature to an absolute viscosity which can be converted to a change oil alert when the oil becomes too thick. Generally, temperature measurements by the thermistor 60 are made from −50° C. to 180° C. Preferably, temperature measurements are made from 0° C. to 150° C., and most preferably, temperature measurements are made near ambient temperature to 120° C.

In operation, the sensor 12 is configured to sense at least one oil viscosity parameter. Preferably, the cantilever 24 extends into the oil flow path 13 so that the oil 11 flowing therethrough exerts pressure upon the pressure receiving portion 32 of the cantilever 24. This pressure causes the legs 30 of the piezo-resistive cantilever 24 to bend, changing the resistivity of the resistive portions 34. The amplification element 14 then creates an output signal 38 indicative of the change in the resistive characteristics of the resistive portions 34 for sensing the oil viscosity parameter. The processor 16 receives and stores the output signal 38 and compares the output signal 38 to a stored resistance value to determine the quality of the oil 11. Finally, the user interface device 18 receives and communicates a lubricating oil quality signal 42 in response to the processor 16 determining quality of the oil 11.

Figure 18:
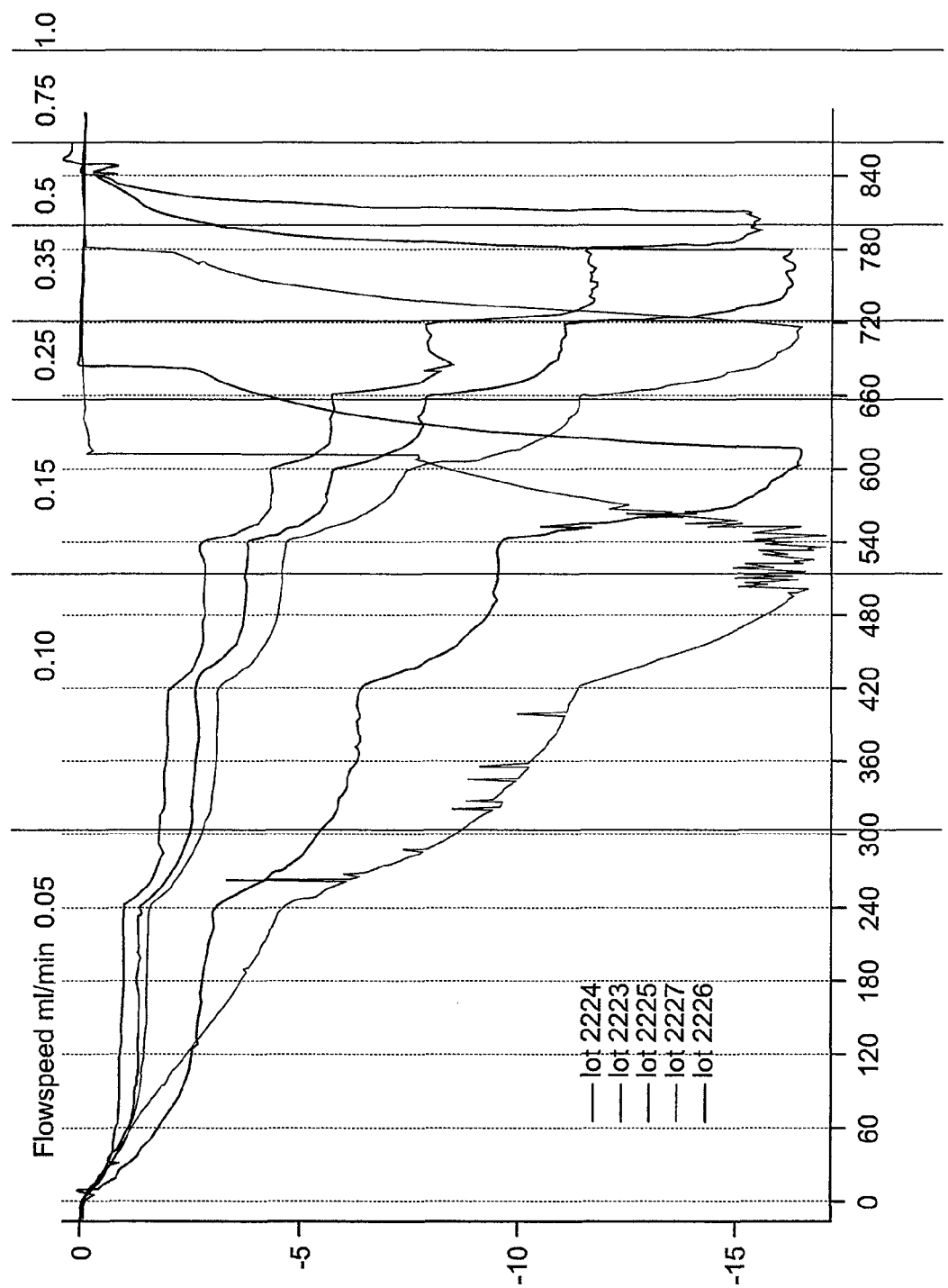
FIG. 18 is a chart illustrating voltage output readings collected by an apparatus of the present invention for different flowspeeds, using a variety of different motor oils.

FIG. 18 illustrates voltage outputs measured by the apparatus 10 for several different commercial motor oils at various flowspeeds. In FIG. 18, Oil #2223 is Exxon® 5W-30, Oil #2224 is Valvoline® 60W, Oil #2225 is Exxon® 20W-50, Oil #2226 is Exxon® 5W-20, and Oil #2227 is Exxon® 10W-40. As described above, the voltage output readings are directly indicative of the deflection of the cantilever 24 of the sensor 12, and are thus indicative of the viscosity of the oil 11.

Figure 3:
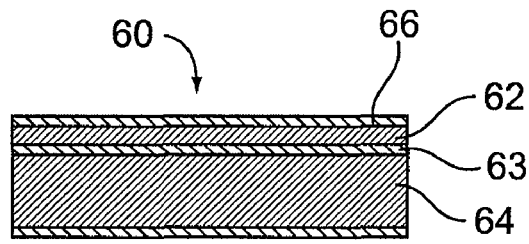
FIG. 3 is a cross-sectional view of a substrate used in manufacturing a sensor of the present invention after a first step of a manufacturing process to manufacture a sensor of the present invention.

The apparatus 10 is preferably manufactured from a substrate 60 that is preferably a silicon-on-insulator (SOI) or single crystal silicon wafer. The manufacturing process described below and illustrated in FIGS. 3-15 uses an SOI wafer, which includes a silicon device layer 62 over a much thicker insulator layer 64, with a masking oxide layer 63 located therebetween. The thickness of the silicon device layer 62 is determined by the desired thickness of the cantilever 24. Since piezo-resistive elements are required to be defined using boron ion implantation, an n-type silicon device layer 60 is used for isolation purpose. A silicon dioxide layer 66 of 1000 Å is thermally grown on the substrate 60 as shown in FIG. 3.

Figure 4:
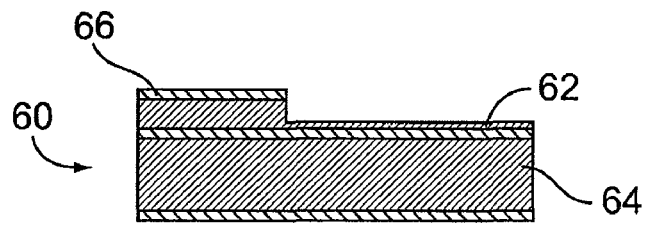
FIG. 4 is a cross-sectional view of the substrate of FIG. 3 after a second step of a manufacturing process to manufacture a sensor of the present invention.

A portion of the surface of the silicon device layer 62 is exposed using standard photolithography process, as shown in FIG. 4. The silicon dioxide layer 66 is etched in buffered hydrofluoric acid with photoresist as a mask and the silicon 62 is etched with dry or wet silicon etches chemistry using oxide as a mask. The targeted thickness of the silicon layer 62 is calculated from the desired spring constant of the chip 22.

Figure 5:
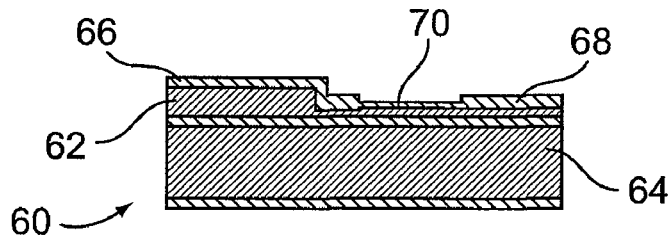
FIG. 5 is a cross-sectional view of the substrate of FIG. 3 after a third step of a manufacturing process to manufacture a sensor of the present invention.
Figure 6:
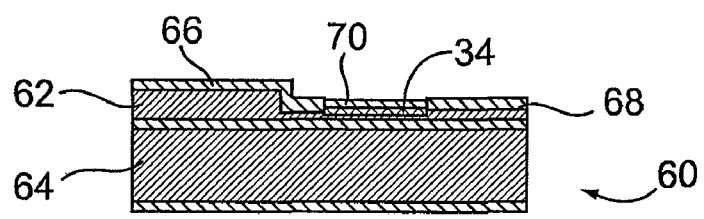
FIG. 6 is a cross-sectional view of the substrate of FIG. 3 after a fourth step of a manufacturing process to manufacture a sensor of the present invention.
Figure 7:
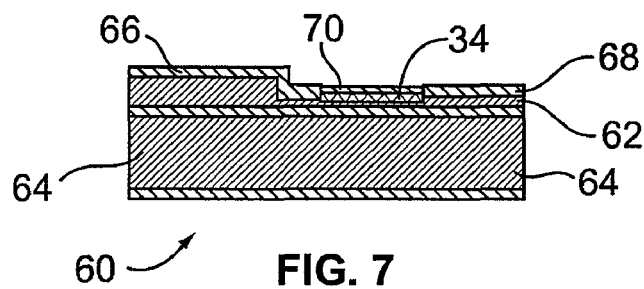
FIG. 7 is a cross-sectional view of the substrate of FIG. 3 after a fifth step of a manufacturing process to manufacture a sensor of the present invention.
Figure 8:
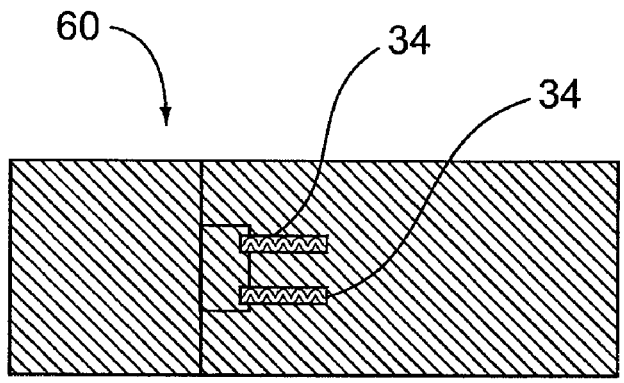
FIG. 8 is a top view of the substrate of FIG. 7.

After the silicon dioxide layer 66 is stripped, a fresh 1 μm thick oxide layer 68 is thermally grown, as shown in FIG. 5. A photolithographic step is performed to pen windows in the oxide layer 68 to facilitate boron ion implantation for piezoresistive assembly. As also shown in FIG. 5, an additional thin (1000 Å) oxide layer 70 is grown primarily to cover the exposed silicon areas before the boron ion implantation is carried out. Then, a boron ion implantation is carried out, illustrated in FIG. 6, followed by a drive-in step at 1000° C. to activate and define the boron resistors 34, illustrated in FIG. 7. FIG. 8 shows a top view of the substrate 60 after the steps of FIGS. 3-7 have been carried out.

Figure 9:
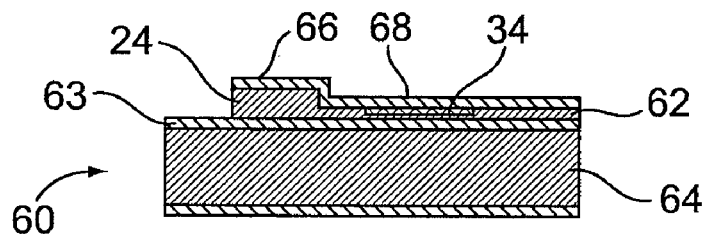
FIG. 9 is a cross-sectional view of the substrate of FIG. 3 after a sixth step of a manufacturing process to manufacture a sensor of the present invention.
Figure 10:
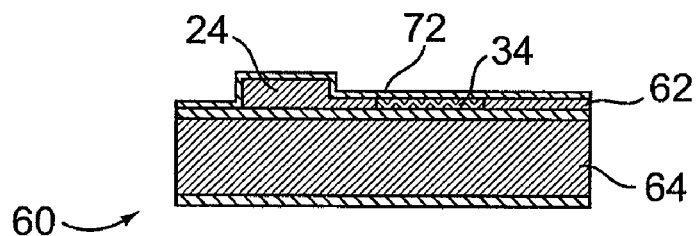
FIG. 10 is a cross-sectional view of the substrate of FIG. 3 after a seventh step of a manufacturing process to manufacture a sensor of the present invention.

Next, the cantilever tip 24 is defined using e-beam photolithography process. A dry etch process is used to etch the silicon layer 62 into the desired cantilever 24 shape, and is stopped at the buried oxide layer 63 of the SOI substrate 60, as shown in FIG. 9. The masking oxide layer 66, 68 is stripped and a fresh layer of oxide 72 is grown to cover all the exposed areas of silicon as shown in FIG. 10.

Figure 11:
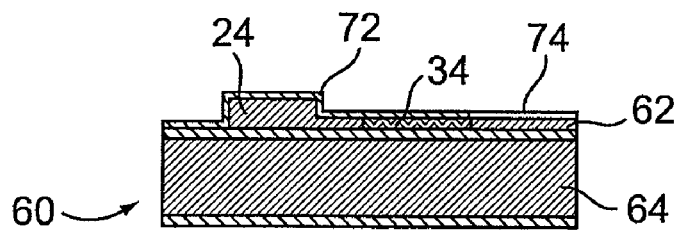
FIG. 11 is a cross-sectional view of the substrate of FIG. 3 after an eighth step of a manufacturing process to manufacture a sensor of the present invention.
Figure 12:
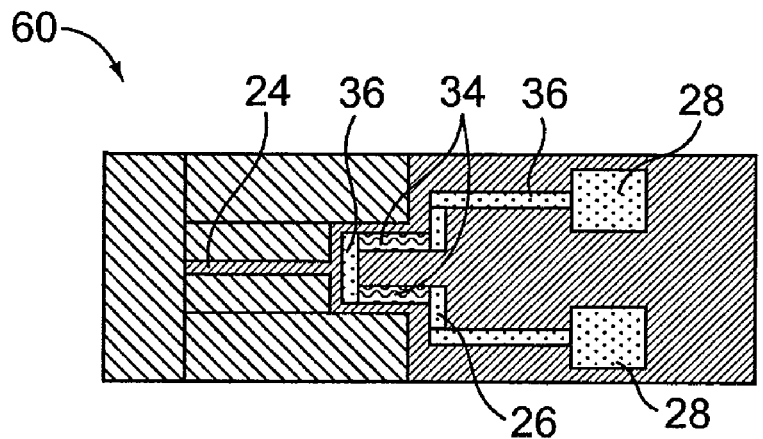
FIG. 12 is a top view of the substrate of FIG. 11.

In the next step, the metal contact pads 28 and the connecting line 36 patterns are defined through a lift-off process step. In this step, a positive photoresist (not shown) covers all areas except the pad 28 and the connecting lines 36. The contact areas are opened by etching the oxide under layer 63, and a metal layer 74 such as aluminum or chromium/gold is deposited. The metal layer 74 can be used to form the pads 28 and the leads 26, and could also be used to form connecting lines 36 to connect the pads 28 and leads 26. The substrate 60 is then dipped in organic solvent, such as acetone, to remove the photoresist. The metal layer 74 covering the photoresist is also lifted in the process. The pads 28, leads 26, and connecting lines 36 are then thereby defined. After these steps are performed, the substrate 60 appears as shown in FIGS. 11 and 12.

Figure 13:
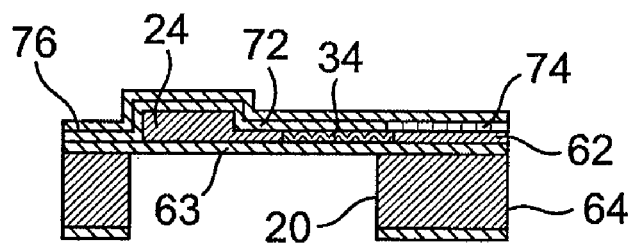
FIG. 13 is a cross-sectional view of the substrate of FIG. 3 after a ninth step of a manufacturing process to manufacture a sensor of the present invention.

The substrate 60 is then flipped over to perform a backside lithography step to integrate the base 20 and cantilever tip 24 into a piezoresistive assembly 12. Using oxide as a mask, the base 20 is etched from the insulator layer 64 in a deep reactive ion etching (DRIE) system while protecting the front side with a layer of photoresist 76. The DRIE process is stopped at the buried oxide layer 63 as shown in FIG. 13.

Figure 14:
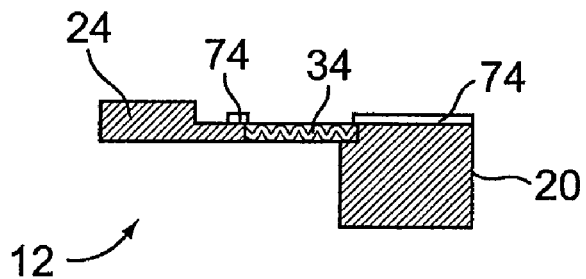
FIG. 14 is a cross-sectional view of a sensor of the present invention after a final step of the manufacturing process of FIGS. 3-13.
Figure 15:
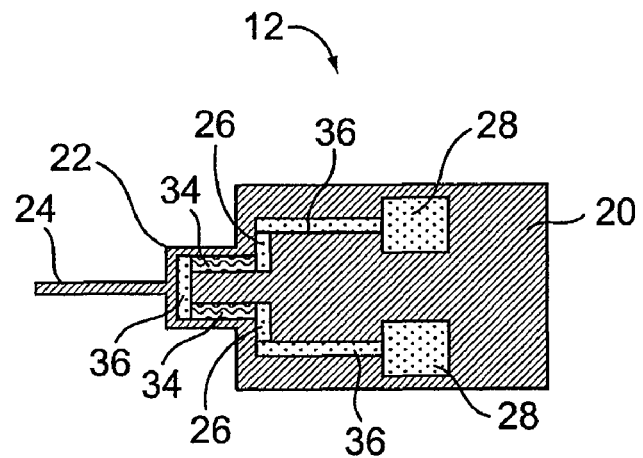
FIG. 15 is a top view of the sensor of FIG. 14.

Finally, the photoresist layer 76 on the front side is removed in oxygen plasma, and the oxide layers 63, 72 are stripped completely to release the completed sensor 12. A cross-sectional view of the completed sensor 12 is shown in FIG. 14, and a top view of the completed sensor 12 is shown in FIG. 15. It is understood that the above process can be modified, either by changing the steps, adding additional steps, or removing steps as desired. It is also understood that the above process is only one method of manufacturing the sensor 12 of the present invention, and other suitable methods can be used as well.

As stated above, the sensor 12 may alternately be manufactured with a carbon nanotube cantilever 124, rather than a silicon cantilever 24, as shown in FIG. 16. To manufacture a sensor 12 having a carbon nanotube cantilever 124, the etching shown in FIG. 9 is done in a different manner, so that a silicon cantilever 24 is not etched. Rather, after the etching is completed, carbon nanotube deposition is performed to deposit the carbon nanotube cantilever 124 in the desired location. Modification of other steps may be necessary as well.

The present invention also includes a method of measuring the viscosity of a lubricating oil 11, which may utilize an apparatus as disclosed above. The method includes a step of sensing an oil viscosity parameter at a piezo-resistive cantilever sensor 12. The sensor 12 receives pressure exerted by the lubricating oil 11 on a cantilever 24 having a pressure receiving portion 32, as the lubricating oil 11 comes into contact with the pressure receiving portion 32. The cantilever 24 has a first resistive portion 34a in electrical communication with the pressure receiving portion 32 and a second resistive portion 34b in electrical communication with the pressure receiving portion 32. An output signal 38 is created, and is indicative of a change in the resistive characteristics of the first and second resistive portions 34 as the lubricating oil 11 comes into contact with the pressure receiving portion 32 for sensing the first oil viscosity parameter. The output signal 38 is amplified at an electrical circuit amplification element 14. The output signal 38 is received and stored at a processor 16 in communication with the electrical circuit amplification element 14. Quality of the lubricating oil 11 is determined by comparing the output signal with a stored resistance value, as illustrated in FIG. 19. A lubricating oil quality signal 42 is received and communicated at an interface device 18 in response to the processor 16 determining quality of the lubricating oil 11. The method may also include the step of driving current through the first resistive portion 34a and the second resistive portion 34b.

In one embodiment, the method includes the steps of receiving the output signal 38 at an RF transmitter 46 in electrical communication with the electrical circuit amplification element 14, transmitting the output signal 38 to the processor 16 at the RF transmitter 46, receiving the output signal 38 from the RF transmitter 46 at an RF receiver 48 in electrical communication with the processor 16, and communicating the output signal 38 to the processor 16 from the RF receiver 48.

In one embodiment, the method includes the steps of receiving the lubricating oil quality signal 42 at a network interface 50 for interfacing with a communication network 52, transmitting the lubricating oil quality signal 42 to the communication network 52, receiving the lubricating oil quality signal 42 from the communication network 52 at the user interface device 18, and communicating the lubricating oil quality signal 42 through the interface device 18. The lubricating oil quality signal 42 can include content of at least one of "change oil now" information, information regarding the time until an oil change is needed, information regarding the driving distance until an oil change is needed, viscosity information, service station information, and/or coupon information, among other types of useful content. In a further embodiment, the method also includes the steps of receiving a plurality of lubricating oil quality signals 42 at an intermediary server 54, determining whether to send service station information and/or coupon information to respective user interface devices 18, associated with each user interface device 18 based on the content of each of the lubricating oil quality signals 42, and transmitting service station information and/or coupon information to respective user interface devices 18 when the determination indicates that the content includes "change oil now" information, the content includes information regarding the time until an oil change is needed which is less than a predetermined time, and/or the content includes information regarding the driving distance until an oil change is needed which is less than a predetermined distance. This process is illustrated in FIG. 19.

The present invention also includes a method of calibrating an apparatus 10 as described above for measuring the viscosity of a lubricating oil 11. First, the piezo-resistive cantilever sensor 12 is positioned in the flow-line or flow path 13 of a calibration oil 11 having a known viscosity value associated therewith. The calibration oil 11 flows through the flow path 13 into the sensor 12, and the apparatus 10 measures the output signal value 38 for the calibration oil 11. The apparatus 10 then stores the output signal value 38 for the calibration oil 11 and also stores the known viscosity value for the calibration oil 11. Once the apparatus 10 is calibrated, then the processor can translate output signals 38 generated by oil 11 in use into viscosity values by comparison to the stored output signal value 38 of the calibration oil 11, which has a known, stored viscosity value. In this embodiment, the output signal value 38 for the calibration oil 11 and the known viscosity value for the calibration oil 11 are retrieved, and then the viscosity of the lubricating oil 11 is calculated using the output signal value 38 for the calibration oil 11 and the known viscosity value for the calibration oil 11, for determining the quality of the lubricating oil 11.

The apparatus 10 and method described above can also be used with other fluids in addition to lubricating oil, including biological fluids. Lubricating oil, as described herein, includes many different oil fluids, such as those that lubricate automotive engines, automotive transmissions, automotive gears, metal-working equipment, hydraulic equipment, equipment requiring grease, oil drilling equipment, heat exchangers, and kitchen appliances. Further, the apparatus 10 can be configured to measure or detect other physical properties of fluids, such as electric field, magnetic field, other viscoelastic properties, fluid mechanics, physical dimensions of solutes, and long range forces such as electrostatic and Van der Waals forces, and/or chemical properties such as chemical nature of solvents and solutes and chemisorption.

Other Embodiments

In another embodiment, illustrated in FIG. 20, the apparatus 10 may include a sensor 112 having a plurality of cantilevers 24. The sensor 112 shown in FIG. 20 has an array of three cantilevers 24 connected to a single chip 22. In one embodiment, the sensor 112 may be configured so that the resistivity of each cantilever 24 is separately measured, with a separate output signal 38 indicative of a change in the resistive characteristics of the resistive portions 34 of each respective cantilever 24. In another embodiment, the sensor 112 may be configured so that the sum of the resistivity of all the cantilevers 24 is measured, with a single output signal indicative of a sum of the changes in the resistive characteristics of the resistive portions 34 of all of the cantilevers 24. In either embodiment, the output signal(s) 38 may be used to obtain an average resistivity of the three cantilevers 24. The use of multiple cantilevers 24 can produce more stable and reliable measurements.

The present invention can also be used to measure properties of a fluid other than viscosity. For example, the present invention can include a magnetic particle detection apparatus 210, a chemical detection apparatus 310, and a capacitance measurement apparatus 410. Each of these apparatuses 210, 310, 410 contains a sensor 212, 312, 412 that reacts to the property of the fluid to be measured. For example, in the viscosity measuring apparatus 10, the sensor 12 reacts by the deflection of the cantilever 24 by the moving oil 11. These additional apparatuses 210, 310, 410 are described below.

The magnetic particle detection apparatus 210, as shown in FIGS. 20-22, includes a magnetic particle detection sensor 212, which detects the presence of magnetic particles in a fluid 11 based on a reaction of the sensor 212 to the magnetic particles. One use of such a magnetic particle detection sensor 212 is to detect the presence of small metal pieces in engine oil that are worn from moving engine components. The sensor 212 can also detect particles of iron oxide, or other magnetic particles indicative of oil quality. In the embodiment shown in FIGS. 20-22, the sensor 212 is substantially the same as the sensor 12 described above, and the apparatus 210 includes a solenoid 280 positioned above the cantilever 224 and a void or chamber 82 between the solenoid 280 and the cantilever 224. Additionally, the cantilever 224 is preferably positioned parallel to the flow path of the oil 11, rather than extending out into the flow path of the oil 11 like the preferred viscosity sensor 12, so that the flow of the oil 11 does not bend the cantilever 224. When power is supplied to the solenoid 280, a magnetic field (B) is created, attracting magnetic particles in the oil 11. As the magnetic particles move toward the solenoid 80, the particles contact the cantilever 224 and cause the cantilever 224 to deflect into the chamber 82. As described above, the cantilever 224 is piezo-resistive, so the deflection causes the resistivity of the resistive portions 34 of the cantilever 224 to change. Greater numbers of magnetic particles in the oil 11 will cause more particles to push against the cantilever 24, causing greater deflection. Thus, the resistivity of the cantilever 224 is indicative of the number, mass, and/or concentration of magnetic particles in the fluid. The magnetic particle detection apparatus 210 may be used to continuously monitor the magnetic particles in the oil 11, or may intermittently monitor the magnetic particles by intermittently supplying power to the solenoid 280. When the power to the solenoid 280 is cut off, the magnetic particles are released.

In this embodiment, the other components of the magnetic particle detection apparatus 210 are substantially the same as those of the apparatus 10 described above. However, the change in resistivity of the cantilever 224 in the magnetic particle detection sensor 212 is indicative of the mass or concentration of magnetic particles in the fluid 11. Thus, the lubricating oil quality signal 42 produced by the apparatus 210 preferably includes the number, mass, or concentration of magnetic particles in the fluid 11, or a similar value.

In an alternate embodiment, the magnetic particle detection apparatus 210 may not contain a solenoid 280. Rather, the cantilever 224 is coated with a magnetic material, for example, Permalloy (FeNi), Permalloy with a protective coating such as chromium or Teflon deposited by chemical vapor deposition, or other such material. Magnetic particles attracted to the magnetic cantilever 224 will deflect the cantilever 224. Since the magnetic material is always present on the sensor 212 (not requiring electric power like the solenoid 280), the sensor 212 does not release the particles and continuously monitors the magnetic particles in the oil 11. Upon saturation (reaching a predetermined calibrated deflection), both the sensor 212 and the oil 11 can be replaced. Still further, as described above, the magnetic particle detection sensor 212 may alternately contain a plurality of cantilevers 224 which may be arranged in an array.

The chemical detection apparatus 310, as shown in FIGS. 20 and 23, includes a chemical detection sensor 312, which detects the presence of one or more chemicals in a fluid 11, based on a reaction of the sensor 312 to the chemicals. The sensor 312 may be used to detect oil contamination components, such as water, ethanol, or ethylene glycol, or to detect the pH of the oil. Similarly to the magnetic particle detection sensor 212 described above, the cantilever 324 of the chemical detection sensor 312 is preferably positioned parallel to the flow path of the oil 11, rather than extending out into the flow path of the oil 11 like the preferred viscosity sensor 12, so that the flow of the oil 11 does not bend the cantilever 324. Also, similarly to the magnetic particle detection sensor 212 described above, the cantilever 324 of the chemical detection sensor 312 is piezo-resistive and has a void or cavity 382 behind the cantilever 324. Generally, the cantilever 324 of the chemical detection sensor 312 contains, or is coated with, a substance that interacts with the chemical that the chemical detection sensor 312 is intended to detect, causing the cantilever 324 to bend. As with the magnetic particle detection apparatus 210, the other components of the chemical detection apparatus 310 are substantially the same as those of the apparatus 10 described above. However, the change in resistivity of the cantilever 324 in the chemical detection sensor 312 is indicative of the presence of the chemical it is intended to detect in the fluid 11. Thus, the lubricating oil quality signal 42 produced by the apparatus 310 preferably includes the amount or concentration of a specified chemical or chemicals in the fluid 11, or the pH of the fluid 11, or a similar value.

In the embodiment shown in FIGS. 20 and 23, the sensor 312 contains an array of three cantilevers 324, each configured to detect a different type of chemical. One such cantilever may be configured to detect water in the engine oil 11, and is preferably coated with a water-absorbing organic polymer for this purpose. As water is absorbed, the polymer coating will swell and increase in mass due to the water absorption, deflecting the cantilever 324. Thus, the amount of deflection (and the change in resistivity) of the water-detecting cantilever 324 directly corresponds to the amount of water present in the oil 11. Other chemical-absorbing coatings, or coatings exposing reactive groups specific to a particular type of chemical contamination, can be used to detect other chemicals in this manner. Another cantilever 324 may be configured to detect ethylene glycol in the engine oil 11, and is preferably coated with a ketone coating for this purpose. Any ethylene glycol in the oil 11 will react with the ketone coating. This chemical reaction changes the surface free energy of the cantilever 324, and this energy change, in turn, causes stress in the cantilever 324, resulting in deflection. Thus, the amount of deflection (and change in resistivity) of the ethylene glycol-detecting cantilever 324 directly corresponds to the amount of ethylene glycol present in the engine oil. Other chemically-reactive coatings can be used to detect other chemicals in this manner. The sensor 312 may also be configured to detect the pH of the engine oil 11. A pH sensor 312 preferably contains two cantilevers 324, each coated with mercaptohexadecanoic acid, hexadecanthiol, or other thiol components, or terminated with carboxylic acid, hydroxyl, and amino groups, to detect changes in pH through protonation-deprotonation events. Such reactions occurring on the coating of the cantilevers 324 change the surface free energy of the cantilever 324, causing the cantilever 324 to deflect, as described above. Thus, the amount of deflection (and change in resistivity) of the cantilevers 324 of the pH sensor 312 directly corresponds to the amount of protonation-deprotonation events and is indicative of the pH of the oil 11.

In other embodiments, the chemical detection sensor 312 may contain a greater or smaller number of cantilevers 324 for any number of chemicals in a fluid 11. Additionally, the chemical detection sensor 312 may be configured to be intermittently activated by inclusion of a mechanical mechanism (not shown) which enables retraction of the chemical detection sensor 312 into a protecting compartment. This mechanical mechanism enables measuring and exposing the sensor 312 to the oil 11 only at specific times.

The capacitance measurement apparatus 410 may also be used in connection with the present invention, including a capacitance sensor 412, based on a reaction of the sensor to changes in capacitance of the oil. A preferred embodiment of the capacitance sensor 412 is shown in FIG. 20, and contains a pair of parallel, spaced metal plates 484 forming a capacitor and wires (not shown) running from each plate to a capacitance measurement device. The plates 484 are electrically insulated from other components, such as components of the viscosity measurement apparatus 10, the magnetic particle detection apparatus 210, and the chemical detection apparatus 310. In one embodiment, the plates 484 are protected with a coating.

The capacitance sensor 412 measures the capacitance (C) of the oil 11, with the purpose of determining the dielectric constant ($\epsilon_r$) of the oil 11. Capacitors are charge-storing devices made up of two plates separated by a distance. Charge stored in the capacitor is proportional to the potential difference (V) between the plates:

$$Q(\text{charge}) = C \times V$$

Because of the polarizing nature of dielectric materials (such as oil), the electric field between the plates is reduced for the same amount of charge on the plates. Measuring the dielectric constant is based on a parallel plate capacitance measurement. The dielectric constant is a material characteristic expressed as the capacitance between two plates when the intervening space is filled with a given insulating material (in the preferred embodiment, oil) divided by the capacitance of the same plate arrangement when the space is filled with air or is evacuated, according to the following equation, where C is the capacitance, Fr is the dielectric constant, $\epsilon_o$ is the permittivity constant of vacuum, A is the plate surface area, and D the separation between the plates:

$$C = \epsilon_r \epsilon_0 A/D$$

Reference capacitance (with air or vacuum between the plates) is determined prior to insertion of the capacitance sensor 412 into the oil 11. Thus, dielectric constant can be easily determined from the capacitance measured by the capacitance measurement apparatus 410. Capacitance can be measured either continuously or intermittently to monitor changes in the dielectric constant.

The dielectric constant changes as oil degrades, due to the presence of impurities often caused by oxidation of the oil 11. Thus, the dielectric constant determined by the capacitance measurement apparatus 410 is indicative of oil quality. Because the dielectric constant of oil also changes with temperature, a thermistor (not shown) is preferably located proximate the capacitance sensor 412 to detect the temperature of the oil 11. This allows the output of the capacitance sensor 412 to be adjusted based on the effect of the temperature of the oil 11. Thus, the lubricating oil quality signal 42 produced by the apparatus 410 preferably includes the dielectric constant of the fluid 11, or a similar value.

As illustrated in FIG. 20, the viscosity sensor 112, the magnetic particle detection sensor 212, the chemical detection sensor 312, and the capacitance sensor 412 are all preferably located on the end of the same dipstick 123. The dipstick 123 preferably has a U-shaped end placed in the flow path of the oil 11, allowing the oil 11 to flow through the gap 186 in the dipstick 123. The viscosity sensor 112, having an array of three cantilevers 24, is positioned at one end of the gap 186. The magnetic particle detection sensor 212 and the chemical detection sensor 312 are positioned proximate the middle of the gap 186, on opposite sides of the gap 186, allowing the oil 11 to flow parallel to the cantilevers 224,324 thereof. The capacitance sensor 412 is positioned at the end of the gap 186 opposite the viscosity sensor 112, so that the plates 484 are positioned in parallel on opposing sides of the gap 186, allowing the oil 11 to flow between. Thus, one dipstick 123 can be configured to enable several different types of measurement according to the present invention.

Benefits

There are many advantages to the present invention. Excessive viscosity can lead to many problems, and detecting fluid viscosity can result in fewer transmission failures in older cars, fewer engine failures, and fewer oil changes. Presence of a significant amount of magnetic particles, such as worn metal pieces, can have a detrimental effect on oil performance. Similarly, excessive impurities, improper pH, or oil degradation can be detrimental to oil performance. All of these measurements enable a user to more accurately determine when changing oil is necessary, and may also alert the user to check for malfunctioning components that may cause these oil problems. Additionally, the extremely small size of the sensor 12 allows for the attachment of the sensor 12 anywhere, such as at the end of a dipstick.

Any process descriptions or blocks in the figures may be understood as representing modules, segments, or portions of code which include one or more executable instructions for implementing specific logical functions or steps in the process, and alternate implementations are included within the scope of the embodiments of the present invention in which functions may be executed out of order from that shown or discussed, including substantially concurrently or in reverse order, depending on the functionality involved, as would be understood by those having ordinary skill in the art.

It will be understood that the invention may be embodied in other specific forms without departing from the spirit or central characteristics thereof. The present embodiments, therefore, are to be considered in all respects illustrative and not restrictive, and the invention is not to be limited to the details given herein.

What is claimed is:

1. An apparatus for measuring the viscosity of a lubricating oil comprising:
    a piezo-resistive cantilever sensor for sensing a first oil viscosity parameter, the sensor comprising:
    a cantilever having a pressure receiving portion for receiving pressure exerted by the lubricating oil as the lubricating oil comes into contact with the pressure receiving portion, the cantilever further having a first resistive portion in electrical communication with the pressure receiving portion and having a second resistive portion in electrical communication with the pressure receiving portion;
    a first lead in electrical communication with the first resistive portion; and,
    a second lead in electrical communication with the second resistive portion;
    an electrical circuit amplification element in electrical communication with at least one of the first lead and the second lead for creating an output signal indicative of a change in the resistive characteristics of the first and second resistive portions as the lubricating oil comes into contact with the pressure receiving portion for sensing the first oil viscosity parameter;
    a processor in communication with the electrical circuit amplification element and having a memory associated therewith for receiving and storing the output signal and for determining quality of the lubricating oil by comparing the output signal with a stored resistance value; and,
    a user interface device in communication with the processor for receiving and communicating a lubricating oil quality signal through the interface device in response to the processor determining quality of the lubricating oil.

2. The apparatus of claim 1 wherein the electrical circuit amplification element is a Wheatstone bridge.

3. The apparatus of claim 1 wherein the electrical circuit amplification element is connected to a power supply for driving current through the first resistive portion and the second resistive portion.

4. The apparatus of claim 1 further comprising:
    an RF transmitter in electrical communication with the electrical circuit amplification element for receiving the output signal and for communicating the output signal to the processor; and,
    an RF receiver in electrical communication with the processor for receiving the output signal from the RF transmitter and for communicating the output signal to the processor.

5. The apparatus of claim 1 further comprising:
    a network interface for interfacing with a communication network for receiving the lubricating oil quality signal and for transmitting the lubricating oil quality signal to the communication network, wherein the user interface device receives the lubricating oil quality signal from the communication network and communicates the lubricating oil quality signal through the interface device.

6. The apparatus of claim 1, wherein the lubricating oil quality signal comprises content of at least one of change oil now information, time until oil change is needed information; distance until oil change is needed information, viscosity information, service station information, and/or coupon information.

7. The apparatus of claim 6 further comprising:
    an intermediary server for receiving a plurality of lubricating oil quality signals, determining whether to send service station information and/or coupon information to respective user interface devices associated with each user interface device based on the content of each of the lubricating oil quality signals, and transmitting service station information and/or coupon information to respective user interface devices when the determination indicates that the content comprises change oil now information, the content comprises a time until oil change is needed information which is less than a predetermined time; and/or the content comprises distance until oil change is needed information which is less than a predetermined distance.

8. The apparatus of claim 1 wherein the cantilever and the electrical circuit amplification element are integrally fabricated within a cantilever chip.

9. The apparatus of claim 8 wherein the piezo-resistive cantilever sensor is mounted to a motor oil dip stick for insertion into an automobile engine.

10. The apparatus of claim 1 wherein the first lead is connection to a first contacting deposited on a ceramic plate, and wherein the second lead is connected to a second contacting deposited on the ceramic plate.

11. The apparatus of claim 10 wherein the first lead electrical circuit element is connected to the first and second leads through first and second pads.

12. The apparatus of claim 10 wherein the first and second pads are at least partially gold, and wherein the first and second leads are at least partially aluminum.

13. A method of measuring the viscosity of a lubricating oil comprising:
    sensing a first oil viscosity parameter at a piezo-resistive cantilever sensor, comprising the steps of:
    receiving pressure exerted by the lubricating oil on the cantilever having a pressure receiving portion, as the lubricating oil comes into contact with the pressure receiving portion, the cantilever further having a first resistive portion in electrical communication with the pressure receiving portion and having a second resistive portion in electrical communication with the pressure receiving portion; and,
    creating an output signal indicative of a change in the resistive characteristics of the first and second resistive portions and the lubricating oil comes into contact with the pressure receiving portion for sensing the first oil viscosity parameter;
    amplifying the output signal at an electrical circuit amplification element;
    receiving and storing the output signal at a processor in communication with the electrical circuit amplification element;
    determining quality of the lubricating oil by comparing the output signal with a stored resistance value; and,
    receiving and communicating a lubricating oil quality signal at an interface device in response to the processor determining quality of the lubricating oil.

14. The method of claim 13 further comprising the step of driving current through the first resistive portion and the second resistive portion.

15. The method of claim 13 further comprising the steps of:
receiving an output signal at an RF transmitter in electrical communication with the electrical circuit element;
transmitting the output signal to the processor at the RF transmitter;
receiving the output signal from the RF transmitter at an RF receiver in electrical communication with the processor; and,
communicating the output signal to the processor from the RF receiver.

16. The method of claim 13 further comprising the steps of:
receiving the lubricating oil quality signal at a network interface for interfacing with a communication network;
transmitting the lubricating oil quality signal to the communications network;
receiving the lubricating oil quality signal from the communication network at the user interface device; and,
communicating the lubricating oil quality signal through the interface device.

17. The method of claim 13 wherein the lubricating oil quality signal comprises content of at least one of change oil now information, time until oil change is needed information; distance until oil change is needed information, viscosity information, service station information, and/or coupon information.

18. The method of claim 17 further comprising the steps of:
receiving a plurality of lubricating oil quality signals at an intermediary server;
determining whether to send service station information and/or coupon information to respective user interface devices, associated with each user interface device based on the content of each of the lubricating oil quality signals; and,
transmitting service station information and/or coupon information to respective user interface devices when the determination indicates that the content comprises change oil now information, the content comprises a time until oil change is needed information which is less than a predetermined time, and/or the content comprises distance until oil change is needed information which is less than a predetermined distance.

19. An apparatus for measuring a property of a lubricating oil comprising:
a piezo-resistive cantilever sensor for sensing a first parameter, the sensor comprising:
a cantilever having a pressure receiving portion for receiving pressure caused by a reaction of the cantilever to the property of the lubricating oil, the cantilever further having a first resistive portion in electrical communication with the pressure receiving portion and having a second resistive portion in electrical communication with the pressure receiving portion;
a first lead in electrical communication with the first resistive portion; and,
a second lead in electrical communication with the second resistive portion;
an electrical circuit amplification element in electrical communication with at least one of the first lead and the second lead for creating an output signal indicative of a change in the resistive characteristics of the first and second resistive portions as the pressure receiving portion receives pressure by a reaction of the cantilever to the property of the lubricating oil, for sensing the first parameter;
a processor in communication with the electrical circuit amplification element and having a memory associated therewith for receiving and storing the output signal and for determining quality of the lubricating oil by comparing the output signal with a stored resistance value; and,
a user interface device for in communication with the processor for receiving and communicating a lubricating oil quality signal through the interface device in response to the processor determining quality of the lubricating oil.

20. The apparatus of claim 19, wherein the property is the amount of magnetic articles in the lubricating oil, and the cantilever reacts by deflecting in response to pressure exerted by the magnetic particles being attracted to a magnetic field.

21. The apparatus of claim 19, wherein the property is the amount of a chemical in the lubricating oil, and the cantilever reacts by deflecting in response to pressure exerted by absorption of the chemical by a chemical-absorbing coating on the cantilever.

22. The apparatus of claim 19, wherein the property is the amount of a chemical in the lubricating oil, and the cantilever reacts by deflecting in response to pressure exerted by a change in the surface free energy caused by a chemical reaction between the chemical and a coating on the cantilever.

23. The apparatus of claim 19, wherein the property is the pH of the lubricating oil, and the cantilever reacts by deflecting in response to pressure exerted by a change in surface free energy caused by a protonation-deprotonation reaction of a coating on the cantilever.

* * * * *